US006809821B2

(12) United States Patent
Thomasson et al.

(10) Patent No.: US 6,809,821 B2
(45) Date of Patent: Oct. 26, 2004

(54) OPTICAL-REFLECTANCE-BASED MASS-FLOW SENSOR

(75) Inventors: J. Alex Thomasson, Starkville, MS (US); Ruixiu Sui, Mississippi State, MS (US)

(73) Assignee: Mississippi State University, Mississippi State, MS (US)

( * ) Notice: Subject to any disclaimer, the term of this patent is extended or adjusted under 35 U.S.C. 154(b) by 264 days.

(21) Appl. No.: 09/796,492

(22) Filed: Mar. 2, 2001

(65) Prior Publication Data

US 2002/0024666 A1 Feb. 28, 2002

Related U.S. Application Data

(60) Provisional application No. 60/186,346, filed on Mar. 2, 2000.

(51) Int. Cl.[7] .......................... G01N 21/00; G01F 13/00
(52) U.S. Cl. ..................... 356/342; 73/861.41
(58) Field of Search ................. 356/336–343; 250/576; 73/204.25, 202.5, 861.02, 861.41, 861.73; 56/30

(56) References Cited

U.S. PATENT DOCUMENTS

| | | | | |
|---|---|---|---|---|
| 5,063,729 A | * | 11/1991 | Fox et al. | 56/30 |
| 5,152,174 A | * | 10/1992 | LaBudde | 73/861 |
| 5,701,172 A | * | 12/1997 | Azzazy | 356/28 |
| 5,825,487 A | * | 10/1998 | Felbinger et al. | 356/338 |
| 5,920,018 A | | 7/1999 | Wilkerson et al. | |
| 6,013,921 A | * | 1/2000 | Moller et al. | 250/573 |
| 6,023,969 A | * | 2/2000 | Feller | 73/204.25 |
| 6,272,935 B1 | * | 8/2001 | Strubbe | 73/861.73 |
| 6,362,880 B1 | * | 3/2002 | Anderson, Jr. et al. | 356/337 |
| 6,369,881 B1 | * | 4/2002 | Wang | 356/28 |
| 6,449,932 B1 | * | 9/2002 | Cooper et al. | 56/10.2 |

OTHER PUBLICATIONS

Durrence, J.S., et al., "Evaluation of Commercially–avialable cotton yield monitors in Georgia field conditions", ASAE Paper No. 98–3106 St. Joseph. MEASAE (1998).
Gvili, M., "Cotton yield sensor produces yield maps", In Proc. Beltwide Cotton Conf., D.A. Richter, ed., pp. 1655–1657, Memphis, TN:National Cotton Council of Am. (1998).
Khalilian, A., et al., Improved sensor mounting technology for cotton yield monitors, ASAE Paper No. 991053 St. Joseph MEASAE (1999).
Thomasson, J.A., et al., "Cotton mass flow measurement experiments with two optical devices", Applied Engineering in Agriculture 15(1):11–17 (1999).
Wilkerson, J.B., et al., "Real–time cotton flow sensor", ASAE Paper No. 94–1054, St. Joseph, MEASAE (1994).

* cited by examiner

Primary Examiner—Frank G. Font
Assistant Examiner—Sang H. Nguyen
(74) Attorney, Agent, or Firm—Piper Rudnick LLP; Steven B. Kelber

(57) ABSTRACT

The present invention relates to a mass-flow sensor that measures the mass flow of conveyed reflective materials, such as cotton, in a stream of air or non-opaque fluid. In particular, the mass-flow sensor of the present invention may be used with a GPS receiver as a cotton yield monitor when mounted on a cotton harvester. It can also be used to measure mass flow of the various cotton component streams in a cotton gin. The mass flow measurements may be made non-intrusively and in real time. The present invention also relates to a method for measuring mass flow using the mass-flow sensor of the present invention.

33 Claims, 2 Drawing Sheets

OPTICAL-REFLECTANCE-BASED MASS-FLOW SENSOR

This application claims priority from U.S. Provisional Patent Application Ser. No. 60/186,346, which was filed on Mar. 2, 2000. The entirety of that provisional application is incorporated herein by reference.

This invention was made with U.S. Government support under Contract No. 99-34409-7598 awarded by the Department of Agriculture. The U.S. Government may have certain rights in this invention.

BACKGROUND OF THE INVENTION

1. Field of the Invention

The present invention relates to an apparatus and method for determining the quantity of material being transported through a passage and, more particularly, to a mass-flow sensor that measures the quantity of reflective bulk material conveyed in an air stream or a non-opaque fluid and a method of using the same.

2. Discussion of the Background

Large quantities of bulk particulate materials such as, for example, agricultural crops, are often transported through ducts, conduits, pipes and the like to an accumulation area for processing or utilization. Often, it is desirable to measure the flow of such material during its transport or the quantity of such material that has been accumulated. Until recently, crop yields have been largely determined on the basis of an entire field, without the ability or the need to obtain information regarding the yields from different locations in a field. Generally, crops were recovered, conveyed to a weighing site and weighed with the transporting vehicle or the container, and the weight of the vehicle or container was subtracted from the gross weight to obtain the amount of product recovered. This process is not dynamic in nature and cannot be adapted to real time collection of data that are necessary for analysis of yields collected from individual field areas.

Systems that can measure crop yields as crops are harvested have previously been used in conjunction with, for example, mobile harvesters. Typically, a mobile harvester simultaneously moves over a field picking crops and stores the picked crops in a receptacle mounted on the harvester. One system involves weighing the crop receptacle and the crops in the receptacle as the harvester moves through the field. Machine dynamics and the large receptacle weight to crop weight ratio, however, lead to serious errors when measurements are made on a real time basis.

A different existing real time measurement system operates by utilizing the fact that certain crops are conveyed to the receptacle by means of an airstream. The airstream is directed in such a manner that the conveyed material impinges on a pressure plate that is connected to a pressure transducer that creates a real time pressure signal indicative of the amount of materials striking the plate. This permits real time determination of the quantity of material that is flowing into the receptacle, with the quantity being proportional to the pressure on the plate. This system is useful because it may be installed on mobile harvesting equipment for the measurement of crop yield as the crops are harvested. This system, however, is not suitable when harvesting certain crops, especially cotton. Cotton and similar crops adhere to the pressure plate, thereby inhibiting the flow of cotton to the receptacle. Additionally, as more cotton accumulates on the pressure plate, inaccurate measurements are taken. Finally, it has been found that the pressure plate system cannot be effectively installed on existing cotton harvesting machinery.

Yet another real time system utilizes optical attenuation of infrared light beams that are projected through the conveying duct. This system requires a combination of emitters and receivers located on opposite sides of the duct. The emitters and receivers must be precisely aligned for the system to work properly. This system, however, is difficult to install. Moreover, this system can suffer from error introduced through stray infrared light, temperature fluctuations and accumulation of material on optical surfaces.

These and other prior art systems, therefore, have several, severe constraints. First, prior art systems are limited in terms of accuracy of measurements. Second, prior art systems are physically complex and difficult to install. Furthermore, residue build-up on sensor surfaces presents a problem with measurement stability in field applications. Specifically, residue builds up on the sensor surfaces, reducing the precision of the measurement of the mass flow and biasing the measurement in favor of higher mass flows over time. Additionally, the prior art considers only overall mass flow and does not take into consideration the various mass components such as, for example, extraneous plant material, that may be present in the flow.

In view of the aforementioned deficiencies attendant with the prior art, it is clear that a need exists for an apparatus and method that can accurately measure the mass flow of conveyed materials without the problems found in prior art systems.

SUMMARY OF THE INVENTION

It is an object of the present invention to provide an accurate mass-flow sensor that is simple in design and easy to install.

It is another object of the present invention to provide a mass-flow sensor that is more accurate than previously developed sensors.

It is yet another object of the present invention to provide a mass-flow sensor that can be implemented for the measurement of individual mass components.

It is a further object of the present invention to provide a mass-flow sensor that is capable of physically maintaining clean surfaces on the sensor.

Additionally, it is an object of the present invention to provide a mass-flow sensor that is insensitive to external temperature fluctuation, accumulation of foreign material on operating surfaces and any possible sources of stray light.

To achieve the foregoing and other objects, there is provided a mass-flow sensor for use with a material transport system, e.g., a crop harvester, that overcomes the difficulties found in existing systems. A typical material transport system generally has a conduit defining a flow passage through which entrained materials are transported between inlet and outlet ends of the conduit in a direction parallel to the longitudinal axis of the conduit. The flow sensor comprises a housing unit that includes one or more light sources positioned to project one or more light beams into the flow passage and one or more detectors positioned alongside the one or more light sources to receive light reflected off the entrained materials. The detectors receive the light and convert it into a generated signal indicative of the level of light reflected. A signal processing circuit is connected to the one or more detectors. The signal processing circuit calculates the quantity of material in the flow passage passing through the light beam(s) as a function of the generated signal and a baseline signal indicative of the amount of light measured when no material is flowing through the one or more light beams.

The mass-flow sensor can be used with, for example, a GPS receiver as a cotton yield monitor when mounted on a cotton harvester. It can also be used to measure the mass flow of the various cotton component streams in a cotton gin. These mass flow measurements are made non-intrusively and in real time.

Additionally, the present invention is a method of determining the quantity, or mass flow, of entrained materials flowing through a material transport system having a conduit defining a flow passage through which entrained materials are transported between inlet and outlet ends of the conduit in a direction parallel to the longitudinal axis of the conduit. The method includes projecting one or more light beams through the flow passage in a direction normal to the longitudinal axis of the conduit. The light is detected as it is reflected off the entrained materials flowing through the flow passage. The light is converted into a generated signal indicative of the level of light reflected. The quantity of material in the flow passage passing through the light beam(s) is then calculated as a function of the generated signal and a baseline signal indicative of the amount of light measured when no material is flowing through the one or more light beams.

Further, the present invention relates to a cleaning system for physically cleaning the surfaces of the mass-flow sensor.

With the foregoing and other objects, advantages and features of the invention that will become hereinafter apparent, the nature of the invention may be more clearly understood by reference to the following detailed description of the preferred embodiments of the invention.

DESCRIPTION OF THE PREFERRED EMBODIMENTS

The present invention relates, in one embodiment, to a mass-flow sensor for use in a material transport system having a conduit defining a flow passage through which entrained materials are transported between inlet and outlet ends of the conduit. As will hereinafter be explained, the mass-flow sensor may be used in a wide variety of harvesting and transport equipment that require transporting materials through a flow passage where it is desirable to measure the quantities of such materials flowing through the passage. Examples of such equipment include any crop or cotton harvester, a cotton gin and any pneumatic line that carries materials from one point to another.

Figure 1:
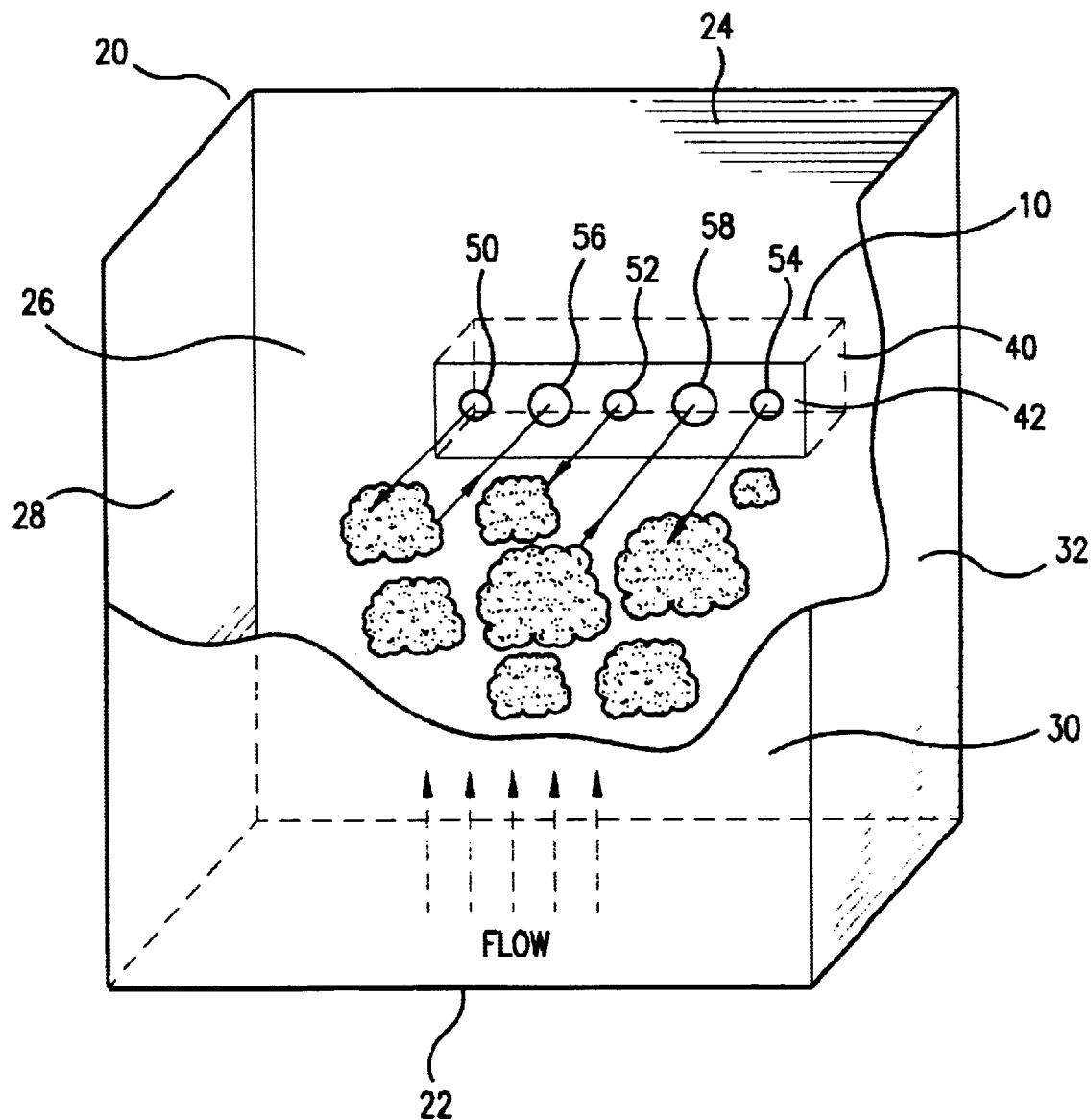
FIG. 1 is a cutaway perspective view of the mass-flow sensor of the present invention mounted, for example, in the conduit of a material transport system.

Referring first to FIG. 1, there is shown a front view of the mass-flow sensor 10 according to the present invention. As illustrated therein, mass-flow sensor 10 is mounted in a conduit, or duct, 20 of a material transport system (not shown). Conduit 20 forms a flow passage through which entrained material, such as cotton, flows from inlet end 22 to outlet end 24 and into a receptacle (not shown). Conduit 20 is illustrated here as having four walls 26, 28, 30, 32, with mass-flow sensor 10 mounted on side wall 26. It will be appreciated that, while mass-flow sensor 10 is shown here mounted on side wall 26, mass-flow sensor 10 may be mounted on any of side walls 26, 28, 30, 32, as well as at other locations inside conduit 20 such as, for example, at inlet end 22 or outlet end 24. Moreover, while the mass-flow sensor of the present invention may be mounted inside the conduit, as shown, it may also be located outside the conduit such as, for example, just beyond the outlet end and before the receptacle into which the materials are being conveyed.

Mass-flow sensor 10 comprises housing unit 40. Mass-flow sensor 10 includes one or more light sources such as light-emitting diodes (LEDs) 50, 52, 54 mounted in housing unit 40. LEDs 50, 52, 54 each project a light beam into the flow passage in a direction normal to the longitudinal axis of conduit 20. LEDs 50, 52, 54 are tuned to the proper wavelength. In a preferred embodiment, LEDs 50, 52, 54 produce light either in the visible or the infrared spectrum; however, use of LEDs that emit light in both the visible and infrared spectra may be desirable, as described in detail below, in applications where impurities such as particles of extraneous material have different reflective tendencies in the different spectra.

Mass-flow sensor 10 also includes one or more photo-diode detectors 56, 58 of appropriate sensitivity (i.e., the detectors need to be sensitive to various ranges of light) mounted in housing unit 40. Thus, LEDs 50, 52, 54 and detectors 56, 58 are contained in a single housing unit 40 mounted in a single location and facing in the same direction (i.e., in one of side walls 26, 28, 30, 32, at either of inlet end 22 or outlet end 24 or outside of conduit 20). Generally speaking, the mass of the entrained materials is determined by measuring the light reflected by the materials. In reflectance measurement circuits, such as used in the present invention, only the light emitted by the light source and reflected by the entrained materials is measured.

A transparent window 42 is located a surface of housing unit 40 between the flow of materials and LEDs 50, 52, 54 and detectors 56, 58. Sensor window 42 protects LEDs 50, 52, 54 and detectors 56, 58 from the entrained materials in conduit 20 as the materials pass by mass-flow sensor 10.

Mass-flow sensor 10 further includes in housing unit 40 a signal processing circuit (not shown) that processes a signal from detectors 56, 58 in such a way that the signal can be acquired and stored by a data acquisition system.

Stray light variations, such as from sunlight, inside conduit 20 and build-up on sensor window 42 such as, for example, dirt, are two factors that may contribute to sensor error. To help alleviate the stray light, frequency-modulated LED light may be used as the light source to illuminate the entrained materials. The mass of the entrained materials, in this case, is determined by measuring the frequency-modulated light reflected by the materials. Light modulation may be accomplished by using a pulse generator (not shown) that generates high-frequency pulses and two driving transistors (not shown) that turn the LEDs on or off according to whether the pulses are high or low, respectively. Only the frequency-modulated light reflected by the entrained materials is measured, thereby eliminating the effect of stray light on sensor accuracy. Another advantage of using a frequency-modulated light source is that it allows the sensor of the present invention to be mounted in a location that eliminates contact between sensor window 42 and the entrained materials, which, in turn, helps alleviate the problem of build-up on sensor window 42. Thus, the mass-flow sensor of the present invention may be mounted at inlet end 22 or outlet end 24 of conduit 20 where sensor window 42 is not in contact with flowing material. In such a position, mass-flow sensor 10 could be exposed to ambient light, but sensor window 42 would not be contaminated, for example, with build-up.

Mass-flow sensor 10 containing both the light sources and the detectors has significant advantages over prior art sensors. First, the requirement for construction materials is reduced because the mass-flow sensor of the present invention requires only a single housing unit for both the light sources and the detectors. This is a significant improvement over the prior art, which requires one housing unit for detectors on one side of the conduit and a second housing unit for light sources on the opposite side of the conduit. Next, the complexity of installation is minimized by using the mass-flow sensor of the present invention. For example, the prior art requires that two ports be cut in a conduit, i.e., one for the unit housing the detectors and one for the unit housing the light sources, instead of one port, or possibly none at all if the sensor is mounted outside the conduit, for the present invention. Moreover, the prior art requires that the light sources and detectors be properly aligned. This creates difficulties in installation and creates the possibility of misalignment over time because of vibration of the sensor. This is not the case, however, with the present invention where the sensors and the light sources are in a single housing unit and, therefore, on the same side of the conduit so that no alignment of two separate housing units is necessary. Most importantly, the accuracy of the mass-flow sensor system is improved with the mass-flow sensor of the present invention. In optical systems using attenuation of a transmitted beam as the principle of measurement, high flows or dense particles can obscure light sources from detectors. When the light is obscured, a sensor registers a signal corresponding to maximum flow. Unlike the prior art, light sources in the present invention are never obscured because light does not have to pass through the conduit to be received by the detectors. Additionally, problems in aligning detectors with light sources reduce precision, as in the prior art. There is no alignment requirement with the present invention because the light sources and detectors are mounted together in a single housing unit. Also, because the mounting position is important to accuracy (e.g., flow tends not to be uniform, so flow is better viewed from certain positions in the conduit than others), the mass-flow sensor of the present invention is more versatile in maximizing placement-related accuracy because the sensor can be mounted at any location on any one of the four sides walls of the conduit, as well as outside the conduit. The prior art, on the other hand, has only two possible mounting configurations, e.g., up-down and left-right.

Instead of measuring the amount of energy, or light, blocked by flowing material as prior art sensors, mass-flow sensor 10 of the present invention measures the amount of energy reflected by the flowing material. In this respect, detectors 58, 60 receive energy reflected back from the conveyed material passing through the flow passage of conduit 20 and convert the energy into a corresponding electrical signal indicative of the amount of energy detected, as explained below. By measuring the amount of energy reflected back to the detectors, the mass-flow sensor of the present invention offers the significant improvements previously discussed, namely reduction in the requirement of constructions materials, minimization of installation complexity and improvement in system accuracy.

The mass-flow sensor of the present invention may also include a means of temperature control. As previously described, the mass-flow sensor uses LEDs as light sources and photodiodes as detectors. While stability of both is very important to sensor accuracy, temperature affects their operation; therefore, a temperature control system may be used to maintain constant temperature inside the mass-flow sensor. Keeping the sensor temperature constant improves sensor accuracy. The temperature control system (not shown) generally comprises a temperature sensor, a reference voltage, a voltage comparator, a solid-state relay and a thermo-electric module. The particular method of maintaining constant temperature inside the sensor (i.e., heating, cooling or a combination of both) is not critical, so long as the temperature inside the sensor remains constant. For example, in operation, a temperature control point is established by setting the reference voltage. If the temperature in the mass-flow sensor is below the temperature control point (as will be the normal case because the control point will typically be set high), the thermo-electric module turns on and raises the temperature of the mass-flow sensor. As the sensor temperature reaches the control point, the thermo-electric module will turn off.

Optionally, a cleaning system may be included in the mass-flow sensor of the present invention. The cleaning system (not shown) generally comprises pressurized air and/or water or cleaning solution. This pressurized air and/or water or cleaning solution is forced across the sensor surfaces, particularly, sensor window 42, at the appropriate time (i.e., when material is not being conveyed such as during the "down time" of the harvester or cotton gin) to clean the sensor surfaces. Instead of compensating for residue build-up on sensor surfaces merely by correcting the electrical signal as the signal baseline changes over time, the mass-flow sensor of the present invention is capable of physically maintaining clean surfaces on the sensor by forcing pressurized air and/or water or cleaning solution over the sensor surfaces. This not only reduces the requirement for maintenance, but also maintains the precision of the original calibration (i.e., the baseline signal).

Additionally, various optical filters (not shown) may be used in front of detectors 56, 58 of mass-flow sensor 10. The use of such filters enables the present invention to account for variations in the proportions of multiple-component flow streams such as when more than one component is present and when those components have significantly different reflectance spectra. For example, seed cotton at harvest contains a significant amount of extraneous plant material. It is known that the ratio of near-infrared reflectance to visible reflectance differs between clean seed cotton and extraneous plant material. Thus, in the case of monitoring trash content in seed cotton, two detector/filter combinations are used, one that is sensitive in the visible range and one that is sensitive in the near-infrared range.

The principle of operation of the present invention is as follows. Light beams from LEDs 50, 52, 54 are directed through the cross section of conduit 20 normal to the longitudinal axis of conduit 20 and the flow of the conveyed material. The light beams illuminate the conveyed material, which reflects energy back to detectors 56, 58 as the conveyed material passes by. Detectors 56, 58 receive the energy and generate a corresponding electrical signal to the data acquisition system, which records and stores the data synchronized with time.

Figure 2:
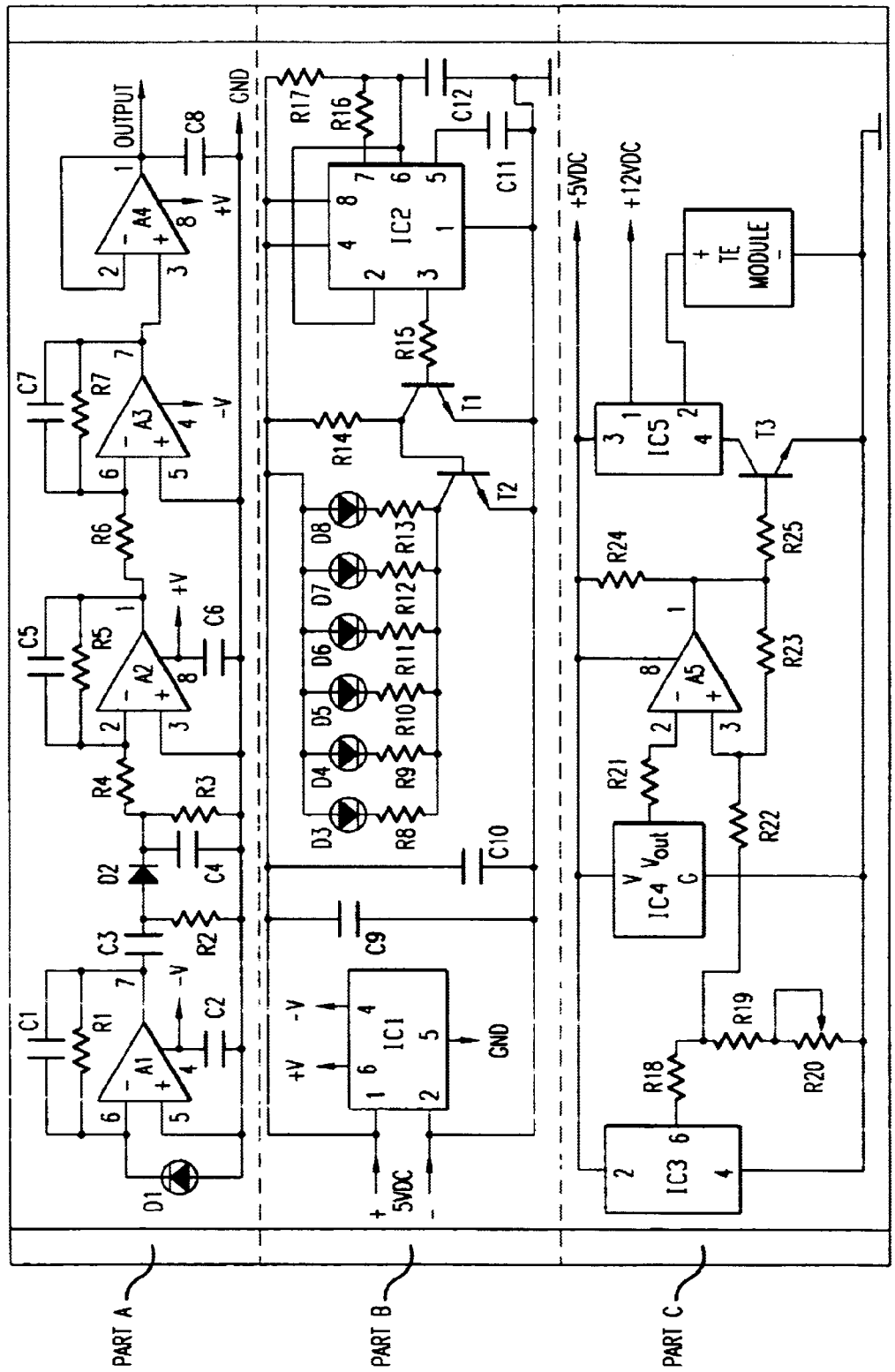
FIG. 2 is a diagram illustrating the signal processing circuit of the mass-flow sensor of the present invention.

The signal processing circuit of the mass-flow sensor of the present invention is shown in FIG. 2. As seen in the circuit diagram therein, the electronic system generally comprises Part A, which is used for reflected light measurement, and may also comprise Part B for generating frequency-modulated light; and Part C, which is for temperature control. Each part will now be discussed in turn.

Part A, reflectance-measurement circuit, is used for measuring reflected light. The reflectance-measurement circuit generally comprises photodiode detector D1, current-to-voltage amplifier circuit A1, an electronic high-pass filter, signal amplifiers A2, A3 and signal follower A4. Photodiode detector D1 detects the light reflected and transforms that light into an electric current. The current, which is proportional to the light intensity, is converted into an electrical voltage with current-to-voltage amplifier circuit A1. Output from current-to-voltage amplifier circuit A1 is followed by a high-pass filter that includes capacitor C3 and resistor R2. The high-pass filter allows only the signal that is generated by frequency-modulated light to pass through, and the signal component generated by non-frequency-modulated light is filtered out. After the high-pass filter, therefore, the signal has no significant component that may be attributed to natural illumination (e.g., sunlight). A demodulation circuit follows the high-pass filter and includes diode D2 for rectification, followed by an RC network for signal integration. After the signal is demodulated, operational amplifiers A2, A3 then amplify the DC signal. Signal follower A4 is used to form a voltage follower to provide stable current drive capacity with relatively low output impedance. The output of amplifier A4 is an analog signal that is proportional to the reflected frequency-modulated light intensity.

Power conversion for Part A and, if used, light modulation, are accomplished in Part B. Circuit IC1 converts an externally-supplied unipolar supply voltage (+5 V) to a bipolar supply (±5 V). This bipolar power supply is required by the amplifiers A2, A3 in Part A. LEDs D3, D4, D5, D6, D7, D8 are modulated by using pulse generator circuit IC2 and two driving transistors T1 and T2. Pulse generator circuit IC2 creates high frequency pulses. Output of pulse generator circuit IC2 drives transistors T1 and T2. Then, LEDs D3, D4, D5, D6, D7, D8, through transistor T2, are turned on or off while the pulses are high or low, respectively. The modulated light is, therefore, produced and may be used as the light source.

The mass-flow sensor of the present invention may further include a temperature control system. If present, then the electronic system includes a temperature control circuit, which is depicted by Part C. The temperature control circuit generally includes temperature sensor IC4, reference voltage circuit IC3, R18, R19, R20, voltage comparator A5, a solid-state relay IC5 and thermo-electric module. A temperature control point is determined by reference voltage circuit IC3, R18, R19, R20. The output of temperature sensor 14 is proportional to the sensor temperature inside the sensor body. Comparator A5 compares the reference voltage from reference voltage circuit IC3, R18, R19, R20 and the output from temperature sensor IC4. If the reference voltage is higher than the temperature sensor output, the output of comparator A5 drives transistor T3 to turn on solid-state relay IC5. In that case, the thermo-electric module is connected to power, and the temperature inside the sensor increases. When the sensor temperature reaches the temperature control point, and the temperature sensor output becomes higher than the reference voltage, then the output of comparator A5 causes transistor T3 to turn off solid-state relay IC5. The thermo-electric module is, therefore, disconnected from power, and the sensor temperature decreases. In this way, the sensor temperature is maintained relatively constant.

Having now fully described the invention, it will be apparent to one of ordinary skill in the art that changes and modifications can be made thereto without departing from the spirit or scope of the invention as set forth herein. Unless such changes and modifications depart from the scope of the invention, they should be construed as being included therein. It is intended, therefore, that the foregoing detailed description be understood from the following claims, including all equivalents, which are intended to define the scope of the invention.

What is claimed is:

1. A mass-flow sensor, comprising:
   at least one light source positioned to project a light beam into a flow passage;
   at least one detector positioned to receive light reflected off entrained materials flowing through the flow passage and to generate a signal indicative of a level of light reflected; and
   a signal processing circuit coupled to the at least one detector, the signal processing circuit being configured to calculate a quantity of material in the flow passage passing through the light beam based on the signal.

2. The mass-flow sensor of claim 1, wherein the at least one light source is a light-emitting diode.

3. The mass-flow sensor of claim 2, wherein the light-emitting diode produces light in the visible spectrum.

4. The mass-flow sensor of claim 2, wherein the light-emitting diode produces light in the infrared spectrum.

5. The mass-flow sensor of claim 1, wherein the light source emits amplitude-modulated LED light.

6. The mass-flow sensor of claim 1, wherein the at least one detector includes a photodiode.

7. The mass-flow sensor of claim 1, wherein at least one detector is positioned alongside at least one light source.

8. The mass-flow sensor of claim 1, wherein the light source and detector are housed in a single housing unit.

9. The mass-flow sensor of claim 1, wherein the contained materials are harvested cotton.

10. The mass-flow sensor of claim 1, further comprising a temperature control system for maintaining a temperature of the detector at a set point.

11. The mass-flow sensor of claim 10, wherein the temperature control system comprises a temperature sensor, a reference voltage, a voltage comparator, a solid-state relay and a thermo-electric module.

12. The mass-flow sensor of claim 1, further comprising a cleaning system.

13. The mass-flow sensor of claim 1, comprising a plurality of light sources and a plurality of detectors, wherein each of the plurality of light sources is positioned to project a light beam into the flow passage and each of the plurality of detectors is positioned to receive light reflected off the entrained materials flowing through the flow passage.

14. The mass-flow sensor of claim 1, wherein the signal processing circuit includes an integrator configured to integrate at least a portion of the signal.

15. A material transport system having a conduit defining a flow passage through which entrained materials are transported, the material transport system comprising a mass-flow sensor comprising at least one light source positioned to project a light beam into a flow passage, at least one detector positioned to receive light reflected off of entrained materials flowing through the flow passage and to generate a signal indicative of a level of light reflected, and a signal processing circuit coupled to the at least one detector and being configured to calculate a quantity of material in the flow passage passing through the light beam based on the signal.

16. The material transport system of claim 15, wherein the light source in the mass-flow sensor is a light-emitting diode.

17. The material transport system of claim 16, wherein the light-emitting diode produces light in the visible spectrum.

18. The material transport system of claim 16, wherein the light-emitting diode produces light in the infrared spectrum.

19. The material transport system of claim 15, wherein the detector of the mass-flow sensor includes a photodiode.

20. The mass-flow sensor of claim 15, wherein at least one detector is positioned alongside at least one light source.

21. The mass-flow sensor of claim 15, wherein the light source and detector are housed in a single housing unit.

22. The material transport system of claim 15, wherein the entrained materials are harvested cotton.

23. The material transport system of claim 15, further comprising a temperature control system for maintaining a temperature of the at least one detector at a set point.

24. The material transport system of claim 15, wherein the light emitting diode emits amplitude-modulated light and the signal processing circuit includes a high pass filter configured to remove portions of the signal corresponding to non-amplitude modulated light.

25. The material transport system of claim 15, wherein the signal processing circuit includes an integrator configured to integrate at least a portion of the signal.

26. A method of determining the quantity of entrained materials flowing through a material transport system having a conduit defining a flow passage, the method comprising:

projecting at least one light beam into the flow passage to contact the materials flowing therethrough;

detecting the light From the light beam reflected off the entrained materials;

generating a signal indicative of the level of light reflected; and calculating the quantity of material in the flow passage passing through the light beam as a function of the signal.

27. The method of claim 26, wherein the light beam is projected by a light-emitting diode.

28. The method of claim 27, wherein the light-emitting diode produces light in the visible spectrum.

29. The method of claim 27, wherein the light-emitting diode produces light in the infrared spectrum.

30. The method of claim 26, wherein the light is detected by a photodiode detector.

31. The method of claim 26, further comprising the step of:

maintaining a temperature of a device utilized in the detecting step at a set point.

32. The method of claim 26, wherein the light beam is amplitude-modulated and further comprising the step of filtering the signal with a high pass filter to remove portions of the signal generated by non-amplitude modulated light.

33. The method of claim 26, wherein the calculating step includes integrating the signal.

* * * * *

UNITED STATES PATENT AND TRADEMARK OFFICE
CERTIFICATE OF CORRECTION

PATENT NO. : 6,809,821 B2
DATED : October 26, 2004
INVENTOR(S) : J. Alex Thomasson et al.

It is certified that error appears in the above-identified patent and that said Letters Patent is hereby corrected as shown below:

Column 5,
Line 54, "detectors 58, 60" should read -- detectors 56, 58 --.
Line 62, "constructions" should read -- construction --.

Column 7,
Line 30, "amplifers A2, A3 in Part A." should read -- amplifers in Part A. --.

Column 8,
Line 32, "contained" should read -- entrained --.

Column 9,
Line 27, "From" should read -- from --.

Signed and Sealed this

First Day of March, 2005

JON W. DUDAS
*Director of the United States Patent and Trademark Office*